(12) United States Patent
Bublewitz et al.

(10) Patent No.: US 9,797,511 B2
(45) Date of Patent: Oct. 24, 2017

(54) PISTON AND CARTRIDGE ARRANGEMENT HAVING SAID PISTON (75) Inventors: Alexander Bublewitz, Herborn (DE); Jens-Peter Reber, Meinerzhagen (DE)

(73) Assignee: Kettenbach GmbH & Co KG, Eschenburg (DE)

( * ) Notice: Subject to any disclaimer, the term of this patent is extended or adjusted under 35 U.S.C. 154(b) by 693 days.

(21) Appl. No.: 13/881,267

(22) PCT Filed: Oct. 26, 2011

(86) PCT No.: PCT/EP2011/068774
§ 371 (c)(1),
(2), (4) Date: Apr. 24, 2013

(87) PCT Pub. No.: WO2012/055921
PCT Pub. Date: May 3, 2012

(65) Prior Publication Data
US 2013/0205988 A1    Aug. 15, 2013

(30) Foreign Application Priority Data

Oct. 26, 2010  (DE) .................... 10 2010 049 378
Feb. 4, 2011   (DE) .................... 20 2011 002 412 U (51) Int. Cl.
*F16J 1/00*    (2006.01)
*A61C 9/00*    (2006.01)
(Continued)

(52) U.S. Cl.
CPC .............. *F16J 1/00* (2013.01); *A61C 9/0026* (2013.01); *B01F 7/00125* (2013.01);
(Continued)

(58) Field of Classification Search
CPC ............................ F16J 1/09; B05C 17/00579
(Continued)

(56) References Cited

U.S. PATENT DOCUMENTS 3,827,538 A * 8/1974 Morgan .................. F16F 9/467
                                                    137/637.3
4,951,848 A * 8/1990 Keller ............... B05C 17/00579
                                                      222/386
(Continued)

FOREIGN PATENT DOCUMENTS

EP      0344491 A1    12/1989
EP      1738834 A1    1/2007
(Continued)

OTHER PUBLICATIONS

Form PCT/IB/338, Notification of Transmittal of Translation of the International Preliminary Report on Patentability.
(Continued)

*Primary Examiner* — Thomas E Lazo
*Assistant Examiner* — Matthew Wiblin
(74) *Attorney, Agent, or Firm* — McDonnell Boehnen Hulbert & Berghoff LLP (57) ABSTRACT

The invention relates to a piston, in particular, for use as a discharge and/or locking piston of a cartridge comprising a base body (25) having a lateral wall provided with sealants (14, 17) and a front-end wall having a vent (21). A locking element (18) is mounted rotatable in the vent (21), whereby a venting channel (23, 24) can be opened or closed by the relative rotation of the locking element (18) in the vent (21). Additionally, the invention relates to a cartridge configuration having such a piston.

11 Claims, 6 Drawing Sheets

(51) Int. Cl.
  *B01F 7/00* (2006.01)
  *B01F 15/00* (2006.01)
  *B05C 17/005* (2006.01)
  *B65D 81/32* (2006.01)
(52) U.S. Cl.
  CPC ...... *B01F 7/00141* (2013.01); *B01F 15/0087* (2013.01); *B01F 15/00909* (2013.01); *B05C 17/00506* (2013.01); *B05C 17/00553* (2013.01); *B05C 17/00576* (2013.01); *B05C 17/00579* (2013.01); *B65D 81/325* (2013.01)
(58) Field of Classification Search
  USPC .................. 92/181 D, 181 R; 222/386, 387; 251/297
  See application file for complete search history.

(56) References Cited

U.S. PATENT DOCUMENTS

| | | | | |
|---|---|---|---|---|
| 5,178,305 | A * | 1/1993 | Keller | B05C 17/00579 222/386 |
| 5,332,124 | A | 7/1994 | Cancro et al. | |
| 5,832,959 | A * | 11/1998 | Szymczakowski | A61M 39/223 137/556 |
| 6,899,254 | B1 * | 5/2005 | Sandholm | B65D 83/0005 222/326 |
| 7,621,428 | B2 * | 11/2009 | Springhorn | B05C 17/00576 222/326 |
| 7,909,211 | B2 | 3/2011 | Springhorn | |
| 2005/0029306 | A1 * | 2/2005 | Brennan | B05C 17/00576 222/327 |
| 2005/0066809 | A1 * | 3/2005 | Nehren | B05C 17/00576 91/422 |

FOREIGN PATENT DOCUMENTS

| | | |
|---|---|---|
| EP | 2116484 A1 | 11/2009 |
| JP | 631112 | 4/1994 |
| JP | 2783463 | 8/1998 |
| WO | 94/14680 A1 | 7/1994 |

OTHER PUBLICATIONS

Korean Office Action (and English translation thereof), Korean Application No. 10-2013-7013176, dated Sep. 4, 2014 (7 pages total).

\* cited by examiner

PISTON AND CARTRIDGE ARRANGEMENT HAVING SAID PISTON

CROSS REFERENCE TO RELATED APPLICATIONS

The present application is a 35 U.S.C. 371 National Application of PCT/EP2011/068774 filed Oct. 26, 2011, which claims priority to German Patent Application No. 102010049378.3, filed Oct. 26, 2010 and German Patent Application No. 202011002412.1, filed Feb. 4, 2011, the entire contents of which are incorporated entirely herein by reference.

The invention relates to a piston, in particular, for use as a discharge and/or locking piston of a cartridge having a base body that has a revolving lateral wall designed as sealing surface, and a front-end wall that has a vent. Furthermore, the invention relates to a cartridge configuration having such a piston.

In the area of dental materials, for example, cartridge-like containers are often used for storing and transporting substances or mixtures of substances, which are filled with the substances, locked by a piston and stored. These cartridges can then also be used for discharging the substances by displacing the piston in the container so that the substance in the container can be discharged through an outlet connection piece as selected, and can be used, for example, in a mixture or directly.

As some substances have a tendency to react with the remaining residual air in the cartridge after the cartridge has been filled and the piston has been inserted, the aim is to let the residual air escape from the cartridge as completely as possible. Possible residual air remaining in the container between the piston and the substance contained in the cartridge is also found to be disadvantageous, because the residual air forms a compressible cap that making the precision of dosing and the application of the substance out of the cartridge more difficult.

For this reason, Sulzer Chemtech AG, CH-8404 Winterthur, has offered a system in which subsequent to filling the cartridge, pistons inserted into it have a central vent so that residual air can escape when the piston is inserted into the cartridge. As soon as the residual air has escaped from the cartridge, the vent is locked by a stopper.

Sometimes, this system is found to be disadvantageous when used, because the high interior pressure within the cartridge can push the stopper out of the vent of the piston. Additionally, using the piston is expensive, as the stopper must be inserted into the piston as a separate component representing an additional work step.

In contrast, the objective of the present invention is to hereby provide a piston as well as a cartridge configuration that enable a release of the residual air and still make a secure and quick locking of the container possible.

According to the invention, this problem is essentially solved by a piston having the feature of Claim 1, and a cartridge configuration having the feature of Claim 13.

A piston according to the invention has a base body that has a lateral wall provided with sealants and a front-end wall which has a vent. This vent extends through the entire base body so that an air exchange is possible between the side of the front-end wall (in feed direction) and the backside of the piston. Thereby, a locking element is mounted rotatable in the vent, whereby a venting channel can be opened and/or closed in the vent by a relative rotation of the locking element. In other words, it is possible to establish and/or prevent the flow connection between the side of the piston in the feed direction and the rear side of the piston.

According to a first embodiment of the invention, the locking element can have a cylindrical outer surface, at least in sections, which has at least one deepening that forms a part of the venting channel. Thereby, the vent has a cylindrical inner surface, at least in sections, in which a protrusion is formed, that is adapted to the deepening in such a way that the protrusion can engage with the deepening to lock the venting channel. Alternatively, it is also possible that the deepening is provided in the cylindrical inner surface of the vent, while the protrusion is provided on the outer surface of the locking element. In both alternatives, the flow connection through the channel is opened when the protrusion does not lie in the deepening and/or the venting channel is locked by bringing the protrusion into the deepening.

According to a second embodiment of the invention, the locking element can be provided with a first locking section having a through hole that abuts a second locking section in the vent that is likewise provided with a through hole. Thereby, the through holes can be brought into alignment in the vent by a relative rotation of the locking element to open the venting channel, or to close the venting channel, the through holes can be misaligned. Thereby, for example, the locking sections can be designed to protrude radially inward and/or radially outward as flange-like sections that are provided with at least one recess and/or with at least one through hole. When the venting channel is open, the residual air can escape from the container through one of the two through holes through the piston.

The vent can be designed in the base body of the piston as a simple through hole, or, for example, tiered with different ranges of diameters that form for example, an adapter for the locking element.

According to one embodiment of the invention, in the front-end wall of the base body of the piston a slot, preferably extending radially can be provided that ends in the vent. Thereby, it is particularly preferred if several slots or recesses of this type are formed in the front-end wall of the base body that run radially toward the vent. The width of the slots is thereby preferably dimensioned in such a way that on the one hand, residual air can easily escape through the slots into the vent while, for example, paste-like or viscous components that are to be discharged with the piston cannot escape, or at best, leak through the slots with difficulty.

Further, the locking element can have a plate or a disk that covers the front-end wall at least in sections. In the front-end wall of the piston, a recess can also be provided that approximately corresponds to the size of the plate or the disk, so that this plate or disk lies at least approximately in one plane with the remaining surface of the front-end wall. If slots are provided in the front-end wall leading to the vent, these also extend through the section covered by the plate or the disk. This plate or disk can improve the venting because the material to be discharged cannot penetrate—or penetrate the slots and/or the vent later.

The sealing effect between the locking element and the base body of the piston can be improved thereby, that these consist of a different soft material. Preferably, the material of the base body is softer than that of the locking element.

Independent of this, the invention is based on the idea that the vent can be sealed by a locking element, which is already tightly retained in the piston when it is, for example, inserted into the open end of a cartridge. Hereby, the residual air shall be able to escape while the piston is being inserted and the vent shall be able to be sealed quickly by actuating the locking element. This can occur, for example, thereby, that the base body is additionally provided with an adapter that is located in the flow direction with the vent, in which the locking element is retained in such a way that by a rotation of the locking element relative to the adapter, a flow connection can be established or broken off between the vent and the venting channel. In other words, the locking element that is affixed non-displaceable in axial direction within the piston can be brought from a position of releasing the vent into a position that locks the vent and the reverse. The locking element can also be mounted by using a threaded connection within the adapter. For this, threaded sections can be provided on the outer surfaces of the locking element.

Thereby, the piston according to the invention differentiates itself due to the advantage that the locking element does not need to be inserted into the piston subsequently. The handling of the piston is consequently made easier because it requires only one rotation of the locking element in order to lock the vent after the residual air has escaped. Furthermore, the locking element also cannot be pushed out of the piston, for example, due to the high interior pressure within the cartridge, because the locking element is securely retained in the base body and is sealed not by an axial motion, but by rotary motion or a rotation.

In a refinement of the inventive idea it is provided that the locking element is retained in the adapter in such a way that the locking element is secured against a motion in a direction pointing away from the vent. This can be accomplished, for example, by a snap-lock connection or snap joint, by means of which the locking element is retained in the adapter.

According to a preferred embodiment of the invention, the locking element is designed essentially cylindrical, whereby the side of the locking element facing the vent has a bottom groove, and on its outer casing surface, at least one lateral groove. The bottom groove and the at least one lateral groove are preferably components of the venting channel through which residual air can escape from the vent into the work environment. The arrangement of the bottom groove and/or the lateral groove can thereby be selected in such a way that the bottom groove can be put in flow connection with the vent and/or that a flow connection between the vent and the bottom groove can be interrupted by a rotation of the locking element within the adapter. Alternatively or in addition to this it is also possible that at least one lateral groove is locked due to the rotation or a flow connection is established with the work environment.

According to the invention, the locking element and/o the adapter can have catch means that make a rotation of the locking element in the adapter more difficult or prevent such in at least one direction of rotation. Hereby, it is possible to prevent an unintentional reverse rotation of the locking element after locking the piston. It is thereby especially preferred when the at least one lateral groove of the locking element and a correspondingly contoured protrusion within the adapter form these catch means so that in addition to the anti-turn protection due to the catch means, the flow connection between the vent and the work environment can simultaneously be interrupted or established.

Alternatively or in addition to this, stop means can be provided in the locking element and/or stop means can be provided in the vent that limit a rotation of the locking element in the vent, in particular, fewer than 180°, preferably fewer than approximately 90°.

The lateral wall that is designed as sealing surface of the piston according to the invention can be provided with at least one sealing lip, at least one ejector bar and/or with one gasket ring that is, for example, retained in a revolving groove. Hereby, it is possible to achieve a reliable gasket seal of the piston and/or within a cartridge. The gasket ring can, for example, be designed as an O-ring or an X-ring.

The cartridge configuration according to the invention has at least one cartridge and a piston inserted in such of the type cited above. Hereby, the cartridge can have an anterior end with an outlet connection piece and a diametrically opposite posterior end that has an adapter opening, which can be locked by the piston.

In the following, the invention will be described in further detail with the aid of an exemplary embodiment, and by referring to the drawing. Thereby, all features described and/or pictorially illustrated are the subject-matter of the invention, independent of their summary in the claims or their reference. Schematically shown are:

Figure 1:
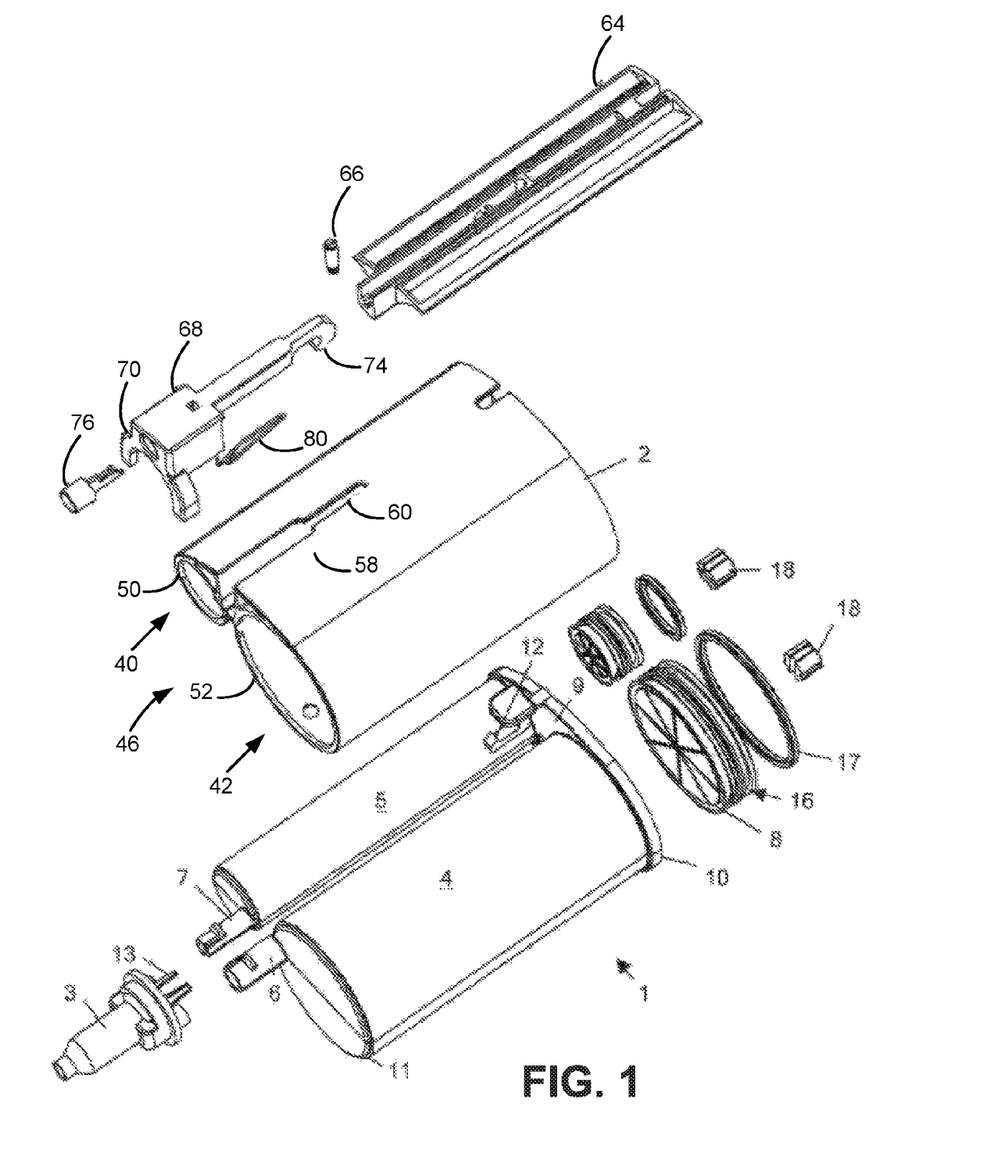
FIG. 1 shows the components of a cartridge configuration according to the invention in an exploded view according to a first embodiment.

The cartridge configuration shown in FIG. 1 has essentially one double cartridge 1 and one support cartridge 2. Double cartridge 1 can thereby be detachably connected with a mixer 3.

Double cartridge 1 essentially consists of two separate storage containers 4, 5, whose housing is essentially designed cylindrically. The anterior end of storage containers 4, 5, shown on the left in FIG. 1 is closed by a front-end wall that is dimensioned sufficiently thick so that it can withstand even high forces when discharging the components. An outlet connection piece 6 or 7 respectively protrudes from this front-end wall that forms a discharge opening of the respective storage container. Outlet connections pieces 6, 7 are located closely adjacent in the illustrated embodiment, i.e. not in the center of the front-end wall of the storage containers. This makes it possible to design mixer 3 comparably compact, as its inlet openings are not required to have much distance between them. On the opposite, posterior side, storage containers 4, 5 are open, so that discharge pistons 8—explained in further detail below—can be inserted into the storage containers for sealing. Discharge pistons 8 simultaneously serve to discharge the substances contained in storage containers 4, 5, for example, components of an impression material or the like, through outlet connection pieces 6, 7.

At their posterior end, storage containers 4, 5 are connected with each other by a bridge 9. Bridge 9 is formed integral with a flange-like edge 10, which projects over the posterior end of storage containers 4, 5. At the anterior end of the two storage containers 4, 5, a revolving groove 11 is provided in the front-end wall, which serves as stop in support cartridge 2.

In the illustrated embodiment, bridge 9 is provided with a catch lever 12, which is designed integral with bridge 9 and storage containers 4, 5. At the anterior end of catch lever 12 in the direction of discharge, a locking latch is provided whose function will be explained in further detail below.

Discharge connection pieces 6, 7 of supply containers 4, 5 can be connected with mixer 3, which is dynamic in the illustrated embodiment, i.e. a powered mixer. For this, the inlet connection pieces of the mixer are inserted into outlet connection pieces 6, 7. Alternatively, it is also possible that the inlet connection pieces of the mixer are adapted around double cartridge 1. At mixer 3, a guiding groove is formed, which projects away from the posterior end of mixer 3 in the direction of double cartridge 1. Each outlet connection piece 6, 7, is provided with a cam whose distance is dimensioned in such a way that the guiding groove of mixer 3 is guided between the two cams when mixer 3 is placed onto outlet connection pieces 6, 7. In the illustrated embodiment, a guide bar is additionally provided on each outlet connection piece 6, 7 that extends in the axial direction and works together with guiding groove of mixer 3. The cams and guiding bars thus facilitate the precise placement of mixer 3 by working together with guiding rib. The insertion of a mixing spindle—not shown—of a discharge device into a corresponding adapter of mixer 3 can be made easier by providing a recess in guiding rib of mixer 3 that makes a view of the adapter of mixer possible that is, for example, designed with an internal hexagon.

In the illustrated embodiment, support cartridge 2 is formed by two integrally connected metal tubes 40, 42, both of which are open. The tubes 40, 42, which consist, for example, of aluminum have a wall thickness of approximately 1 mm to 2 mm, in particular, approximately 1.3 mm. In FIG. 1 at the left anterior end 46, these tubes 40, 42 of support cartridge 2 are—at least in sections—provided with inward-projecting collars 50, 52, which can work together with groove 11 of double cartridge 1 in order to support double cartridge 1 in support cartridge 2. Beyond that, the length of double cartridge 1 is adapted to the length of support cartridge 2 in such a way that bridge 9 or the flange-like edge 10 at the posterior end of double cartridge 1 abuts at the posterior end of the respective tube of support cartridge 2 when double cartridge 1 is inserted into support cartridge 2. As a result, double cartridge 1 is supported and secured in the feed direction of discharge piston 8 at both of its ends in support cartridge 2.

Alternative to the illustrated embodiment, support cartridge 2 can be provided with a front-end wall that replaces the inward-projecting collar, or is supported by it. Such a front-end wall or plate can also be screwed into or glued into support cartridge 2. As the result of a front-end wall, double cartridge 1 is supported even better by support cartridge 2. The wall can either have openings that make the penetration of outlet connection pieces 6, 7 possible, or the wall itself can be provided with connections that can accommodate outlet connection pieces 6. 7.

Additionally, each tube 40, 42 of support cartridge 2 is provided with a window through which double cartridge 1 is visible from the outside. This also makes it possible to identify, for example, a color marking or a similar coding on double cartridge 1 through the window.

In support cartridge 2, in a section 58 between the two tubes 40, 42, a groove 60 is provided for receiving an adapter rail 64. The adapter rail 64 can be slid into this groove 60 and can be fixated there with a screw 66. The adapter rail 64 can, just like support cartridge 2, consist of metal, in particular, aluminum, or preferably of plastic.

Further, support cartridge 2 can be provided with a retaining clip 68 that can be hinged rotatable at a hinge joint in the adapter rail 64. The retaining clip has 68 an approximately U-shaped retaining section 70 that can encompass sections of mixer 3 and thereby fasten it on outlet connection pieces 6, 7. By using a catch hook 74, the retaining clip 68 can be fastened in the adapter rail 64 or support cartridge 2 in its position that fixates mixer 3. In order to deviate the retaining clip 68 from its locked position extending approximately parallel to the tubes of support cartridge 2 into a position releasing mixer 3, an unlocking knob 76 is provided that can deviate the catch hook 74 into a position releasing the lock. As the result of a spring 80 that is indicated in FIG. 1, after actuating the unlocking knob 76, the retaining clip 68 can automatically deviate into the position, in which a replacement or the assembly of mixer 3 is possible. Further, in the adapter rail 64 or in support cartridge 2 a catch protrusion is provided which reaches behind catch lever 12 of double cartridge 1 when it is inserted into support cartridge 2. Hereby, double cartridge 1 is also secured against the feed direction of discharge pistons 8 within support cartridge 2. To remove double cartridge 1 from support cartridge 2, a user must apply pressure to the upper section of catch lever 12 to release the catch mechanism again.

Figure 2:
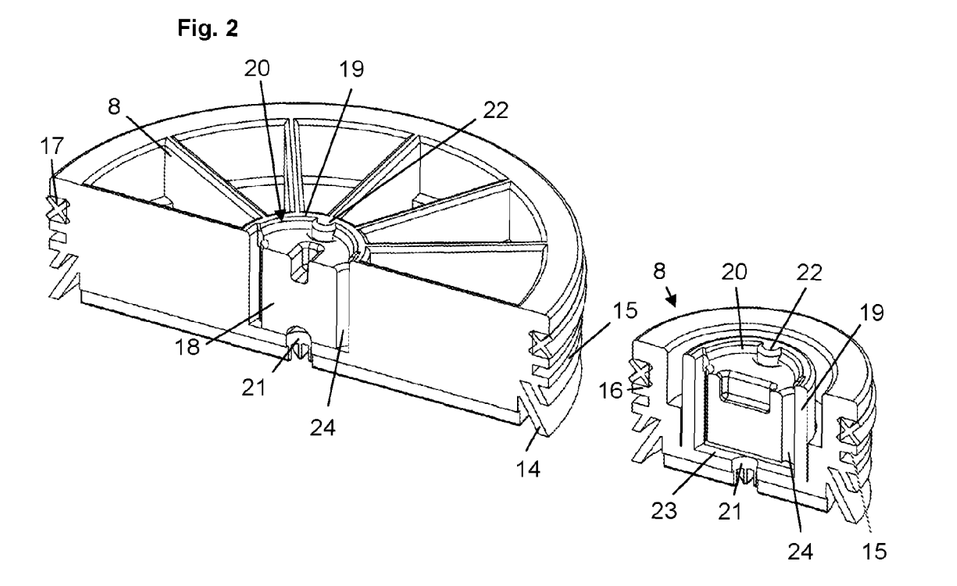
FIG. 2 shows the discharge pistons of the cartridge configuration according to FIG. 1.

As shown in FIG. 2, discharge pistons 8 respectively have an approximately cylinder-disk-like base body with two integrally molded sealing lips 14 and two ejector bars 15, which revolve around the exterior circumference of the discharge pistons. Additionally, a gasket ring 17 is retained in a revolving groove 16 that can, for example, be designed as an O-ring or as an X-ring. In this way, the discharge piston can be displaced on the inner wall of the cartridge while sealed.

A venting channel extends in each discharge piston 8, which can be sealed by a turn-lock closure 18. For this, each discharge piston has an essentially cylindrical or pot-like adapter 19 for a turn-lock closure 18. At its upper edge, this adapter has a bead 20 in FIG. 2, which prevents a movement of turn-lock closure 18 in the axial direction. In this way, at very high discharge forces of a discharge device (dispenser) and the counter pressure of the dental mass that is connected with it, it is prevented that turn-lock closure 18 is pushed axially backward again out of the discharge piston. Otherwise, this would lead to leakage and thus to contamination of the discharge device. Alternative to bead 20, a threaded or a bayonet connection can also be provided between adapter 19 and turn-lock closure 18.

Cylindrical adapter 19 is connected with the interior of supply containers 4, 5 by a vent 21. Further, in the illustrated exemplary embodiment, at two diametrically opposite sides, catch protrusions 22 are provided on the inner side of cylindrical adapter 19.

Figure 3:
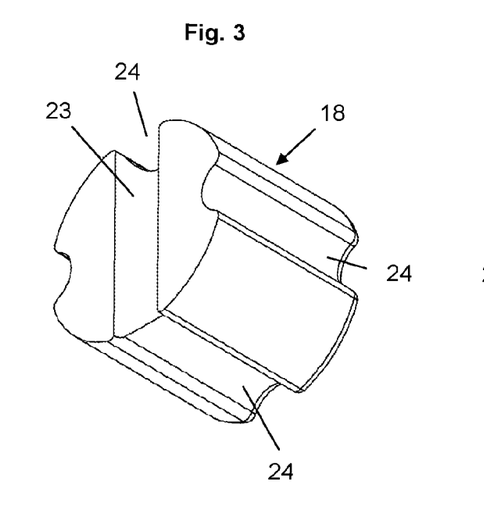
FIG. 3 shows a turn-lock closure of a discharge piston according to FIG. 2.
Figure 4:
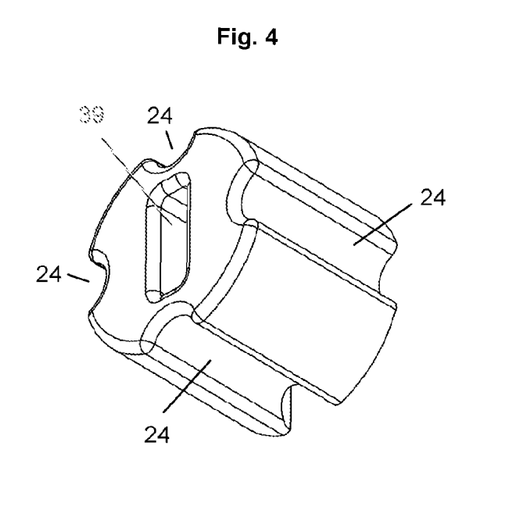
FIG. 4 shows a turn-lock closure in a further perspective view according to FIG. 3.
Figure 5:
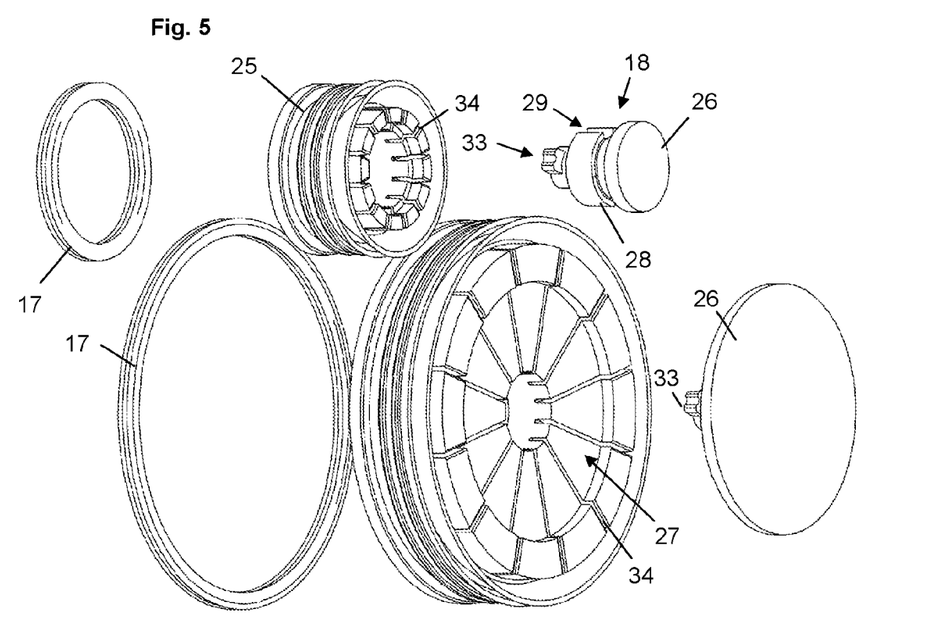
FIG. 5 shows the components of two pistons according to the invention as per a second embodiment.
Figure 6:
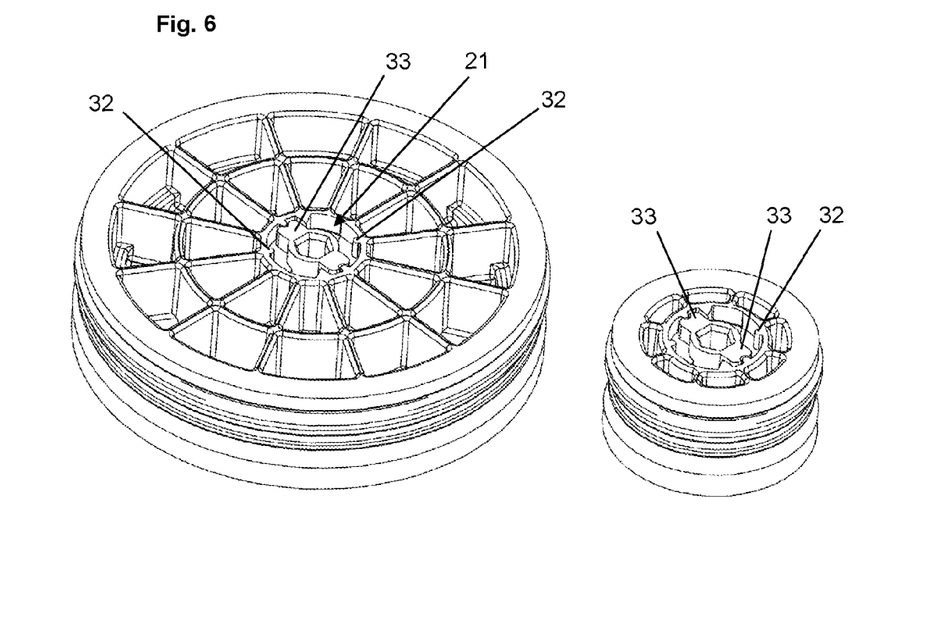
FIG. 6 shows the top side of the pistons according to FIG. 5 in a perspective view.
Figure 7:
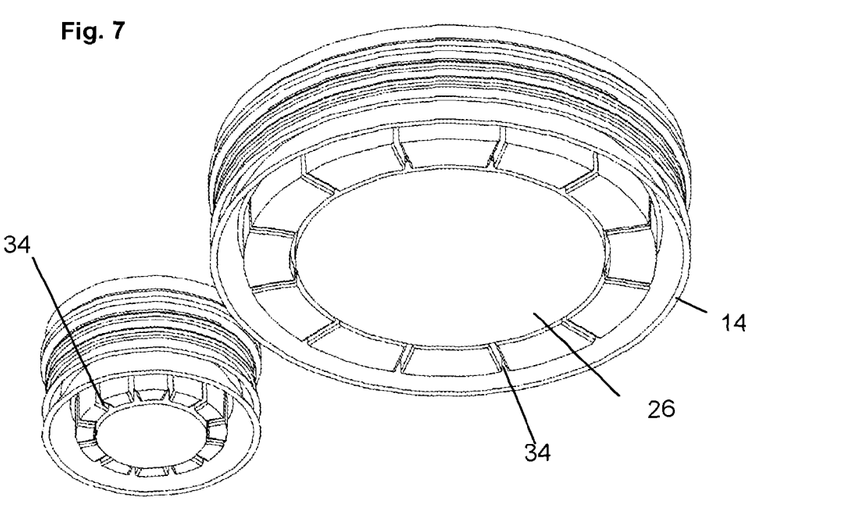
FIG. 7 shows the bottom side of the pistons according to FIG. 5 in a perspective view.

The turn-lock closures 18 shown in detail in FIGS. 3 and 4 are provided respectively with a bottom groove 23 on the bottom side in FIG. 2 and four lateral grooves 24 that extend in axial direction, of which respectively two are connected with bottom groove 23, while the two remaining lateral grooves 24 are not connected with bottom groove 23. On the side opposite to bottom groove 23, each turn-lock closure 18 has a slot 39, for example, in order to rotate the turn-lock closure in the cylindrical adapter by using a tool. Catch protrusions 22 on the inner side of cylindrical adapter 19 thereby prevent an unintentional rotation of turn-lock closures 18.

In the discharge piston on the right in FIG. 2, the two lateral grooves 24 that are not connected with bottom groove 23 engage with catch protrusions 22 so that the two lateral grooves that are connected with bottom groove 23 form a venting channel via vent 21 that is connected with the interior space of supply containers 4, 5.

In contrast, in the left discharge piston in FIG. 2, turn-lock closure 18 is rotated by 90° so that the two lateral grooves 24 connected with bottom groove 23 are locked by catch protrusions 22. In this way it is possible to first let the residual air escape after filling supply containers 4, 5 and inserting discharge pistons 8, and then seal them completely by actuating turn-lock closures 18.

In FIGS. 5 to 9, a second exemplary embodiment of a piston is illustrated whereby the same components have the same reference numbers relative to the previous embodiment. Piston 8 thereby also has a base body 15 with a vent 21 and sealants in the form of a sealing lip 14 and a gasket ring 17 provided in the lateral wall. Locking element 18 of piston 8 is likewise designed as a turn-lock closure, whereby different from the previously described embodiment, a plate 26 is provided at locking element 18. In the state of use of the piston that is shown in FIGS. 6 to 9, it is located on the bottom side of piston 8 in a deepening 27 of the front-end wall of the base body.

Figure 8:
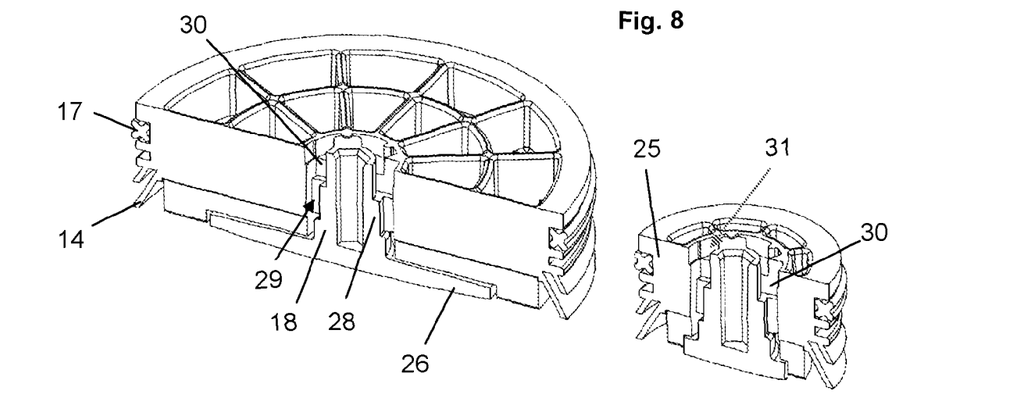
FIG. 8 shows the pistons according to FIG. 5 in open position in partially cross-sectional perspective.
Figure 9:
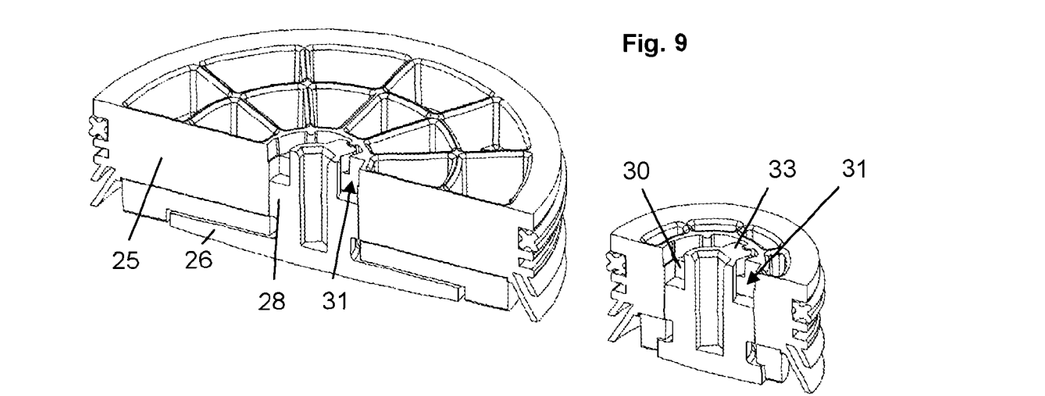
FIG. 9 shows the pistons according to FIG. 5 in closed position in partially cross-sectional perspective.

According to FIGS. 5 to 9, turn-lock closures 18 extend essentially completely through vent 21, or base body 25 of pistons 8. Thereby, on the outer side of a section housed in vent 21 of the respective turn-lock closure 18, a revolving protrusion 28 is designed that forms a locking section. In it, a through hole 29 is provided that extends in axial direction of locking element 18 through locking section 28. Even in the section of vent 21, a radially inward-directed protrusion 30 is formed in base body 25 that likewise forms a locking section and is provided with a through hole 31. As can be seen in FIGS. 8 and 9, the two protrusions 28 and 30 abut. By a corresponding alignment of locking element 18 within vent 21, through holes 29 or 31 of the two protrusions can be aligned to release a venting channel through which residual air can escape through piston 8.

To prevent an unintentional rotation of locking element 18 within base body 25, catch protrusions 32 are formed in vent 21 that work together with corresponding catch elements 33 of locking element 18 in such a way that in order to rotate locking element 18 relative to base body 25, i.e. for opening or closing of the vent, a certain resistance must be overcome.

Furthermore, in the illustrated embodiment, several slots 34 are also formed in the front-end wall of base element 25 that extend in radial direction and end in vent 21. Slots 34 thereby also extend in the section of deepening 27, which is covered by plate 26 of locking element 18. The width of slots 34 is dimensioned in such a way that the residual air can escape into vent 21 through slots 34, but that the leakage of, for example, viscous or paste-like components is made difficult or prevented.

A third embodiment similar to the second embodiment is shown in FIGS. 10 to 13, whereby in turn the same components use the same reference numbers relative to the previous embodiment.

Pistons 8 according to the third embodiment differentiate themselves from those of the second embodiment essentially in the structure of vent 21, and the corresponding outer surface of locking element 18. Thus, on the inner surface of vent 21, a revolving protrusion 35 is formed that engages with a corresponding groove 36 in locking element 18 in order to lock them together. Protrusion 35, as well as groove 36 are respectively provided with through holes 31 or 29, that can be aligned in order to release a venting channel, or misaligned in order to close the venting channel.

Figure 10:
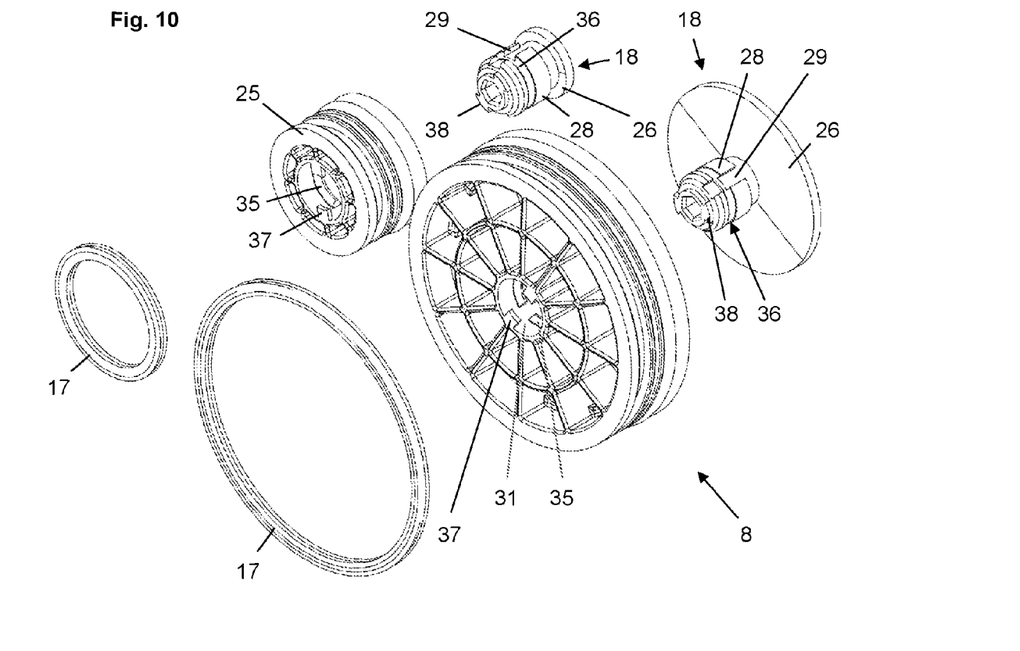
FIG. 10 shows the components of two cartridges according to the invention in an exploded view according to a third embodiment.
Figures 11, 14:
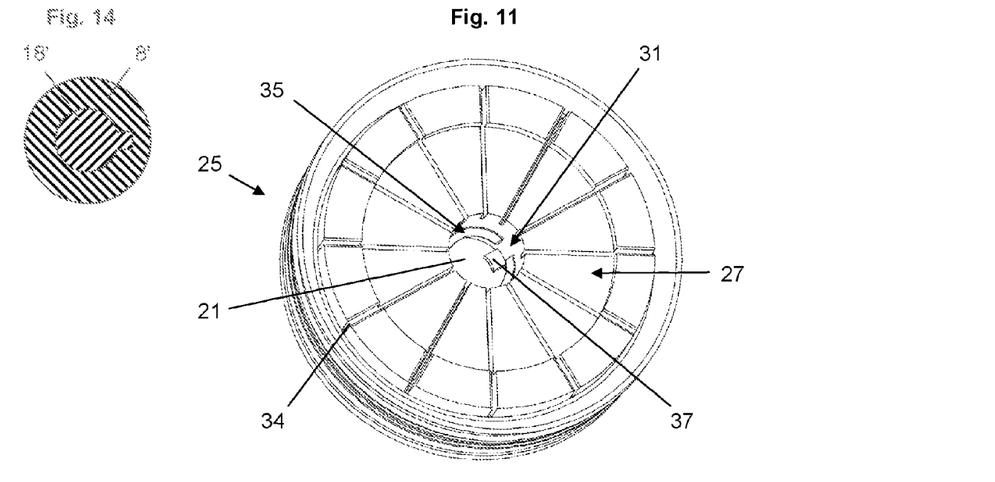
FIG. 11 shows the bottom side of a piston according to FIG. 10.
FIG. 14 shows a schematically sectional view of a discharge piston 8' and a turn-lock closure 18'.

In the illustrated embodiment, each of the two locking elements 18 is respectively provided with two diametrically opposite through holes 29 that are designed as axially extending groove-like recesses within revolving cylindrical protrusion 28. Thereby, through holes 29 extend through groove 36 that is perpendicular to it, which can be slightly deeper than through hole 29, so that protrusion 35 can securely lock through holes 29.

The possibility of rotating locking element 18 within base body 25 to open or close the venting channel, is limited by catch elements 37 in the section of vent 21 of base body 25 in the third embodiment, which work together with corresponding counter catch elements 38 of locking element 18. In the illustrated embodiment, locking element 18 can be rotated by approximately 60° to approximately 120° within base body 25, preferably approximately 90°.

Figure 12:
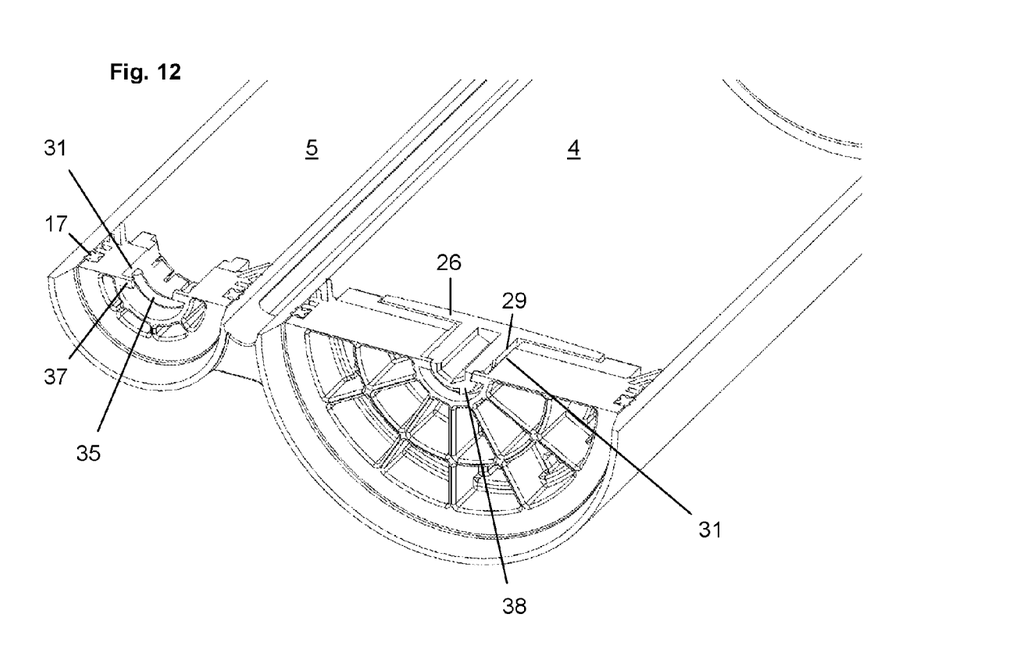
FIG. 12 shows the pistons according to FIG. 10 in a cartridge in open position in a partially cross-sectional perspective.
Figure 13:
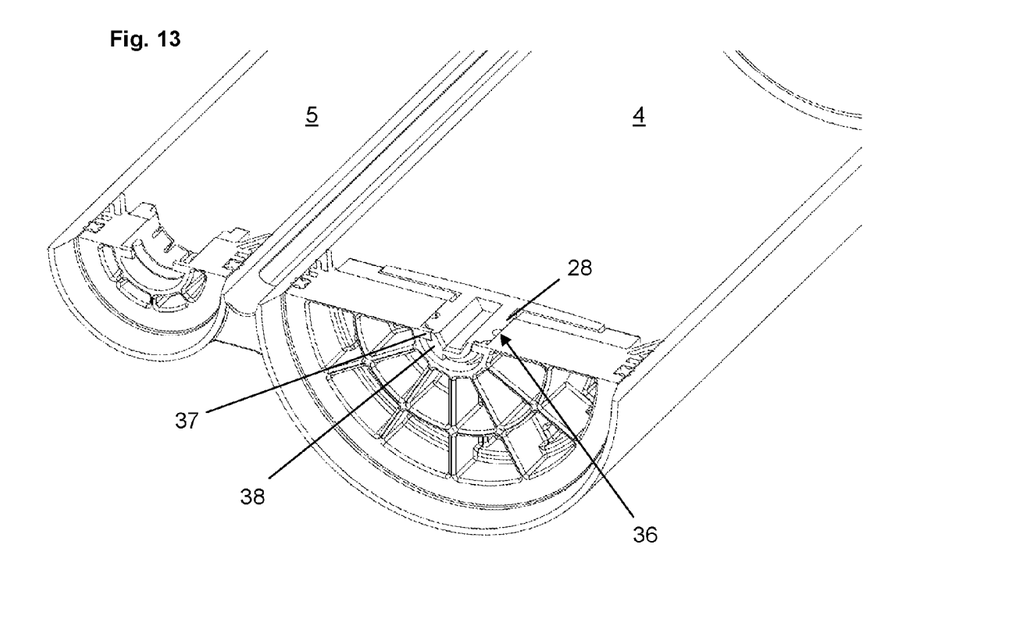
FIG. 13 shows the pistons according to FIG. 10 in a cartridge in closed position in partially cross-sectional perspective.

FIGS. 12 and 13 show pistons 8 respectively inserted in supply containers 4, 5 of a double cartridge, whereby in the smaller left piston, locking element 18 was omitted for reasons of clarity. Hereby, it can be seen that the cross section plane extends through diametrically opposite through holes 31 in protrusion 35 of the respective vent 21.

Thereby, in FIG. 12 locking element 18 is aligned in such a way that the two diametrically opposite through holes 29 that end in revolving slot 36 or go through it, respectively form—together with through holes 31—a venting channel connecting the interior of the respective supply container with the work environment. In other words, the two axially extending groove-like through holes 29 in locking element 18 in the section of groove 36 that revolves perpendicular to it, are not locked by protrusion 35.

In contrast, FIG. 13 shows a state in which locking element 18 is rotated within base body 25 contrasting with FIG. 12 by approximately 90° so that protrusion 35 interrupts the two axially extending, groove-like through holes 29 in locking element 18 in the section of groove 36 that revolves perpendicular to it, and locks it in a sealing manner. Thus, in the state shown in FIG. 13, neither air nor, for example, the paste-like components contained in the respective supply containers 4, 5, can escape from such into the work environment.

REFERENCE NUMBERS

1 Double cartridge
2 Support cartridge
3 Mixer
4, 5 Storage container
6, 7 Output connection pieces
8 Discharge piston
9 Bridge
10 Range-like edge
11 Groove 12 Catch lever
13 Guiding rib
14 Sealing lip
15 Ejector bar
16 Groove
17 Gasket ring
18 Turn-lock closure
19 Adapter
20 Bead
21 Vent
22 Catch protrusion
23 Bottom groove
24 Lateral groove
25 Base body
26 Plate
27 Deepening
28 Protrusion (locking section)
29 Through hole
30 Protrusion (locking section)
31 Through hole
32 Catch protrusion
33 Catch element
34 Slot
35 Protrusion
36 Slot
37 Catch
38 Counter catch

What is claimed is:

1. A piston, for use in a cartridge having a base body that has a lateral wall provided with seals, said piston comprising:
   a vent located in a front-end wall;
   a locking element rotatable mounted in the vent,
   whereby a venting channel can be opened or closed in the vent by a relative rotation of the locking element,
   wherein the locking element has a first locking section having a through hole that abuts in the vent at a second locking section that is likewise provided with a through hole,
   whereby the through holes can be aligned in the vent by a relative rotation of the locking element to open the venting channel, and misaligned to close the venting channel, and
   wherein the locking element is retained in the vent in such a way that the locking element is prevented from a movement in a direction pointing away from the front-end wall.

2. A piston as recited in claim 1,
   wherein the locking element has at least in sections a cylindrical outer surface in which at least one deepening is designed that forms a part of the venting channel, and
   that the vent has a cylindrical inner surface and at least one protrusion is formed that is adapted to the deepening in such a way that the protrusion engages with the deepening to close the venting channel.

3. A piston as recited in claim 2,
   wherein on a front of the locking element that faces the front-end wall, a bottom groove is provided that is a component of the venting channel.

4. A piston as recited in claim 1
   wherein the vent has at least in sections a cylindrical inner surface in which at least one deepening that constitutes a part of the venting channel is formed, and
   that the locking element has at least in sections a cylindrical outer surface in which at least one protrusion is formed that is adapted to the deepening in such a way that the protrusion engages with the deepening for locking the venting channel.

5. A piston as recited in claim 1,
   wherein the locking element is retained in the vent by a catch or snap-in connection.

6. A piston as recited in claim 1,
   wherein the locking element or the vent are provided with catch means that make a rotation of the locking element in the vent more difficult in at least one direction of rotation.

7. A piston as recited in claim 1,
   wherein the locking element or the vent have catch means that limit a rotation of the locking element in the vent, in particular to fewer than 180°.

8. A piston as recited in claim 1,
   wherein at least one radially extending slot is provided in the front-end wall that ends in the vent.

9. A piston as recited in claim 1,
   wherein the base body consists of a softer material than the locking element.

10. A combination of a piston as recited in claim 1 and a cartridge configuration having at least one cartridge that has an anterior end with an outlet connection piece and a diametrically opposite posterior end that has an adapter opening locked by the piston.

11. A piston having a base body that has a lateral wall provided with sealants and a front-end wall having a vent
    wherein in the vent a locking element is mounted rotatable,
    whereby a venting channel can be opened or closed in the vent by a relative rotation of the locking element, and
    wherein the locking element is affixed non-displaceable in axial direction within the piston and can be brought from a position of releasing the vent into a position that closes the vent and the reverse.

* * * * *